(12) United States Patent
Kato et al.

(10) Patent No.: US 6,648,837 B2
(45) Date of Patent: Nov. 18, 2003

(54) MEDICAL GUIDE WIRE

(75) Inventors: Tomihisa Kato, Nagoya (JP); Satoshi Nagano, Nagoya (JP)

(73) Assignee: Asahi Intec., Ltd., Aichi-Ken (JP)

( * ) Notice: Subject to any disclaimer, the term of this patent is extended or adjusted under 35 U.S.C. 154(b) by 0 days.

(21) Appl. No.: 09/884,913

(22) Filed: Jun. 21, 2001

(65) Prior Publication Data

US 2002/0198468 A1 Dec. 26, 2002

(51) Int. Cl.$^7$ ................................................. A61B 5/00
(52) U.S. Cl. ........................................................ 600/585
(58) Field of Search ............................... 600/434, 435, 600/585

(56) References Cited

U.S. PATENT DOCUMENTS

| | | | |
|---|---|---|---|
| 4,538,622 A | 9/1985 | Samson et al. | 128/772 |
| 4,619,274 A | 10/1986 | Morrison | 128/772 |
| 4,748,986 A | 6/1988 | Morrison et al. | 128/772 |
| 4,922,924 A * | 5/1990 | Gambale et al. | 600/585 |
| 5,147,317 A | 9/1992 | Shank et al. | 604/164 |
| 5,281,203 A * | 1/1994 | Ressemann | 600/585 |
| 5,365,942 A | 11/1994 | Shank | 128/772 |
| 5,480,382 A | 1/1996 | Hammerslag et al. | 604/95 |
| 5,891,055 A | 4/1999 | Sauter | 600/585 |
| 5,951,496 A | 9/1999 | Willi | 600/585 |
| 5,957,903 A | 9/1999 | Mirzaee et al. | 604/282 |
| 6,066,100 A * | 5/2000 | Willard et al. | 600/585 |
| 6,428,512 B1 * | 8/2002 | Anderson et al. | 604/170.01 |

FOREIGN PATENT DOCUMENTS

| | | |
|---|---|---|
| DE | 198 23 414 A1 | 6/1999 |
| EP | 495 299 A1 | 7/1992 |
| EP | 879 616 A1 | 11/1998 |
| JP | 59-16649 | 2/1984 |
| JP | 4-25024 | 4/1992 |
| JP | 4-292175 | 10/1992 |
| JP | 6-11339 | 2/1994 |

* cited by examiner

*Primary Examiner*—Max Hindenburg
(74) *Attorney, Agent, or Firm*—Morgan Lewis & Bockius LLP

(57) ABSTRACT

In medical guide wire (1A), a tapered second helical spring (7) is interposed continuously between a first helical spring (6) and the third helical spring (8) each wound around a leading end portion (2). From a middle portion of the second helical spring (7) to a leading top end of the first helical spring (6), a spiral blood stream path (10) is serially provided along a line gap (C1) of the helical springs (7, 6). A gap-stopper (12) is provided between the leading end portion (2) and the second helical spring (7) in order to induce a high speed spiral blood flow (17) along the spiral blood stream path (10) when the leading end portion (2) reaches a diseased area (13). The high speed spiral blood flow (17) provides the leading end portion (2) with the advancing force (F) and the rotational force (T).

3 Claims, 5 Drawing Sheets

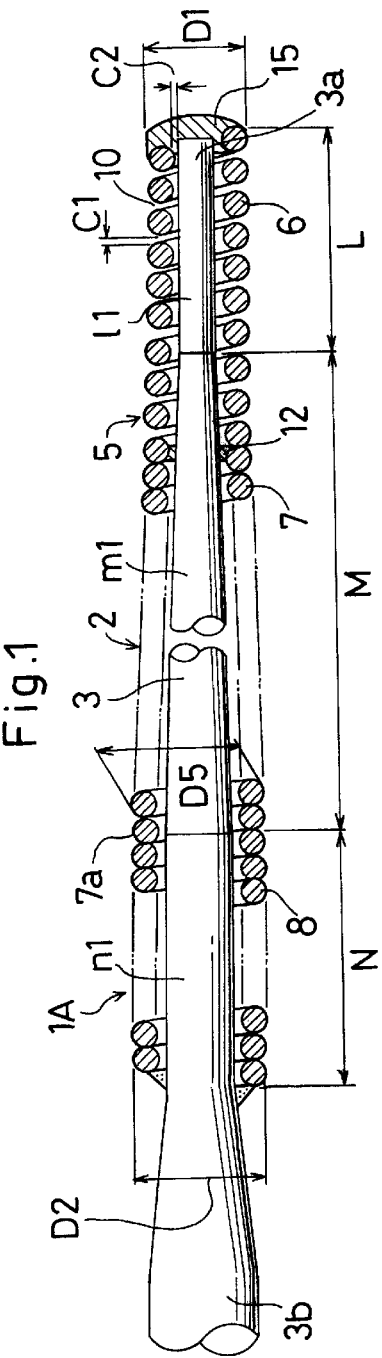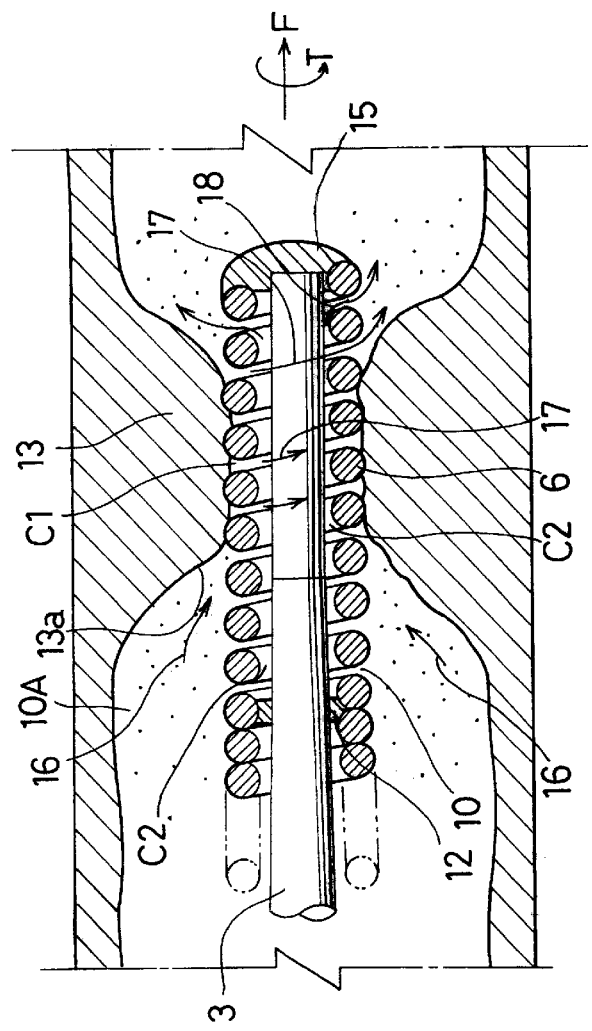

MEDICAL GUIDE WIRE

BACKGROUND OF THE INVENTION

1. Field of the Invention

The invention relates to a medical guide wire which introduces a cathether when inserting it into a blood vessel system to cure vascular strictures or the like.

2. Description of Prior Art

Upon implementing an arteriography, a medical guide wire has been used as a flexible line member to insure that a catheter is inserted when introducing the catheter to a blood vessel system or applying a balloon catheter to a clogged portion of the coronary artery for a treatment purpose. These are illustrated by Japanese Provisional Patent Publication Nos. 4-25024 and 4-292175.

The medical guide wire requires a great degree of flexibility and axial load resistant property (anti-buckling property) against the direction in which the guide wire is inserted, in order to smoothly advance the guide wire into a complicatedly turned blood vessel system or a bifurcated blood vessel system.

The guide wire further requires an appropriate torsional rigidity and a good maneuverability (mechanical properties) to enable an operator to manipulate the direction in which the guide wire advances into the blood vessel system since the manipulator advances a leading end of the guide wire while rotating it outside the blood vessel system.

As a basic structure, the guide wire has a very thin wire at the leading end around which a main helical spring is fit. In order to secure a good mechanical property with the guide wire, a diameter-reduced helical spring is further placed around a leading top end of the main helical spring ("tapered helical spring structure") as shown by Japanese Laid-open Utility Model Application No. 59-16649 and Japanese Provisional Patent Publication No. 6-11339.

However, the guide wire hinders a good blood flow when reaching the leading end to a vascular stricture area although the mechanical property is somewhat improved.

Further, it is necessary for the manipulator to remotely manipulate a handle grip outside the blood vessel with the turning and pushing actions accompanied when advancing and indwelling the leading end to/on the vascular stricture area.

This manipulation requires a considerably high degree of experienced skills to smoothly control the guide wire remotely. In order to smoothly manipulate the guide wire, it is also indispensable to strictly consider a rupture resistant property against a strong torsional torque, the torsional rigidity, the axial load resistant property and the good maneuverability (mechanical properties).

Therefore, the present invention has made with the above drawbacks in mind, it is a main object of the invention to provide a medical guide wire which enables a manipulator to smooth manipulation with a good torsional rigidity, an axial load resistant property and a good maneuverability.

SUMMARY OF THE INVENTION

According to the present invention, there is provided a medical guide wire comprising: an elongated flexible core member, around a leading end portion of which a helical spring is loosely fit; a spiral blood stream path provided continuously between line elements of the helical spring from a middle portion to a leading top end of the helical spring; and a gap-stopper provided at a gap between a line element of the helical spring and the core member in order to introduce a blood flow into the spiral blood stream path at the gap-stopper toward the leading top end of the helical spring.

According to other aspect of the present invention, there is provided a medical guide wire comprising: an elongated flexible core member, around a leading end portion of which a helical spring is loosely fit; the helical spring having a first helical spring having a first line diameter and a second helical spring having a second line diameter smaller than the first line diameter, the first helical spring and the second helical spring being alternately placed around the core member concentrically to form a multi-wound helical spring; and a spiral blood stream path being formed on an outer surface area of a line element of the second helical spring between line elements of the first helical spring, the spiral blood stream path beginning from a middle portion to a leading top end of the helical spring.

The basic concept of the invention is to utilize the fluid characteristics of the blood streams flowing along the blood vessel system. When the medical guide wire reaches its leading end at the stricture area within the blood vessel system, an appropriate amount of the blood flow is secured and maintained by the spiral blood stream path without clogging the blood vessel.

Due to the dynamic pressure from the blood flow, a rotational force and advancing force are provided with the leading end of the medical guide wire.

The phrase "the helical spring loosely fit around the core member" includes states that the helical spring loosely fit its inner surface into an outer surface of the core member when the core member is circular in cross section, and that the helical spring circumscribes its inner surface with the outer surface of the core member when the core member is rectangular in cross section.

The phrase "the helical spring loosely fit around the core member" includes the known "tapered helical spring structure" in which the tapered helical spring is placed between the diameter-reduced helical spring and the diameter-increased helical spring. Further, the phrase "the helical spring loosely fit around the core member" includes the helical spring, a helical diameter of which is uniform through its entire length.

With the spiral blood stream path continuously provided between the line elements of the helical spring (or defined on the outer surface of the helical spring), an appropriate amount of blood flow can be secured and maintained within the blood vessel system when the medical guide wire inserts and indwells its leading end portion to/on the vascular stricture area. This is true when the medical guide wire exceedingly narrows the gap between the leading end portion and the vascular stricture area, or when the medical guide wire gets its leading end portion stuck in the vascular stricture area.

When the guide wire reaches its leading end portion at the vascular stricture area from the normal blood vessel area, the blood stream area around the leading end portion decreases to quicken the blood streams. The quicken blood streams run along the spiral blood stream path to induce the dynamic pressure. The dynamic pressure provides the leading end portion with the advancing force and the rotational force.

Even under the circumstances in which the advancing force and the rotational force are induced in the normal blood vessel area due to the dynamic pressure albeit slightly, the slightly induced forces are resultantly added to the advancing force and the rotational force when the medical guide wire is inserted to indwell its leading end portion to/on the vascular stricture area. This increases the movability of the leading end portion to secure a smoother manipulation, while at the same time, reducing the manipulating force transmitted to a middle portion of the medical guide wire so as to ease the strict mechanical properties required for the medical guide wire.

With the gap-stopper provided between the helical spring and the core member, the gap-stopper acts as a blood stream weir to prevent the blood streams from flowing rearward along the leading end portion of the medical guide wire. The rearward prevention insures the required amount of the blood stream and reinforces the advancing force and the rotational force with which the spiral blood stream path provides the leading end portion.

With the spiral blood stream path and the tapered leading end portion each provided with the medical guide wire, the medical guide wire advances its leading end portion into the vascular stricture area without oscillating the leading end portion approached to the vascular stricture area.

Since the medical guide wire generally provides its leading Lop end with the semi-spherical or semi-spherically shaped head plug in order to smoothly insert the leading top end into the blood vessel system, Karman vortex street appears in front of the semi-spherical head plug when the head plug is straightly subjected to the high speed blood streams. The Karman vortex street induces to oscillate the head plug, and brings the disadvantage to hinder the leading end portion from advancing into the multiple type of the vascular stricture area (eccentric type, irregular type, complicated type, oblong type or the like).

As opposed to the above structure, most of the blood flows along the spiral blood stream path prevents the Karman vortex street from being induced when the leading top end encounters the high speed blood streams. This obviates the harmful oscillation to stabilize the leading end portion, and thereby making it easier to advance the leading end portion into the vascular stricture area.

Considering the spiral blood stream path to act as a minute lead pitch of the helical spring fit into the core member, a secondary advantage is obtained that the spiral blood stream path can be used as a "lubrication pool groove" when applying a lubrication agent on the leading end portion in order to facilitate the insertion into the blood vessel system.

BRIEF DESCRIPTION OF THE DRAWINGS

Preferred forms of the present invention are illustrated in the accompanying drawings in which:

FIG. 1 is a longitudinal cross sectional view of a leading end portion of a medical guide wire according to a first embodiment of the invention;

FIG. 2 is an enlarged longitudinal cross sectional view of the leading end portion of the medical guide in use;

DETAILED DESCRIPTION OF THE PREFERRED EMBODIMENTS

Figure 3:
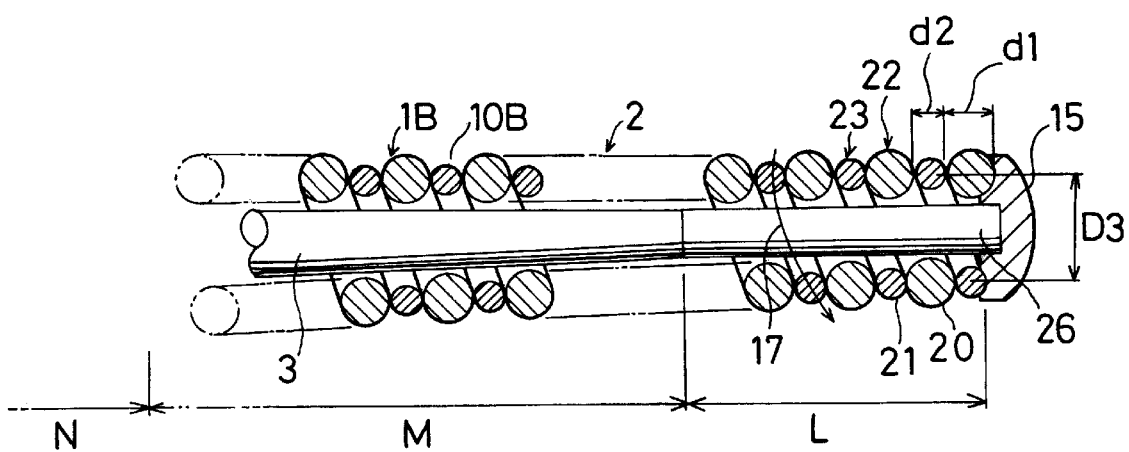
FIG. 3 is a longitudinal cross sectional view of a leading end portion of a medical guide wire according to a second embodiment of the invention.

Referring to FIGS. 1 and 2 which show a first embodiment of the invention, a medical guide wire 1A has a flexible and thin elongated core 3. The elongated core 3 has a leading end portion 2 into which a helical spring 5 is wound so that a space appears between a leading end portion 3 and the helical spring 5.

The helical spring 5 has a first helical spring 6 having a uniformly decreased helical diameter (D1) and a second helical spring 7 consecutively connected to the first helical spring 6 which has a helical diameter (D5) progressively increasing from the leading end 3a to a rear portion 3b of the elongated core 3. To a diameter-increased end 7a of the second helical spring 7, consecutively connected is a third helical spring 8 which has a uniformly increased helical diameter (D2).

Lengthwise sections L, M and N denote where the first, second and third helical springs 6, 7, 8 are in turn situated, and the elongated core 3 has an equi-diametrical thin portion (11), a tapered portion (m1) and an equi-diametrical thick portion (n1) consecutively in the axial direction.

Due to the intermediary presence of the second helical spring portions 7, these helical spring portions 6, 7 and 8 run continuously to provide a tapered structure in which the helical spring portion 5 decreases its diametrical dimension proressively toward the leading end portion 2 of the elongated core 3.

An annular gap-stopper 12 is provided at a predetermined position (e.g., a middle portion) of the second helical spring 7 in order to close a gap (C2) between an outer surface of the elongated core 3 and specified line element of the second helical spring 7.

From the gap-stopper 12 toward a leading top end of the leading end portion 2, there is provided a minute line gap (C1) continuously between neighboring line elements of the second helical spring 7 and the first helical spring 6 (along a lead pitch) in order to define a spiral blood stream path 10. The other part of the line elements of the helical spring 5 than the above are tightly wound.

In this instance, the gap-stopper 12 liquid-tightly connected the between the elongated core 3 and the specified line element of the second helical spring 7 by means of a soldering, an adhesive or the like.

When the medical guide wire 1A reaches its leading end portion 2 at the vascular stricture area 13 (referred simply to as "diseased area") as shown in FIG. 2, the medical guide wire 1A gets the leading end portion 2 stuck in the diseased area 13, or leaves a very thin gap with an inner wall 13a of the diseased area 13. This quickens the blood flow 16 under a decreased blood passage 10A streaming around the leading end portion 2. The quickened blood flow 16 runs along the spiral blood stream path 10 to form a high speed spiral blood flow 17. Although a part of the spiral blood flow 17 occupies the gap (C2), the gap-stopper 12 acts as a blood weir to prevent the spiral blood flow 17 from running rearward in order to form a forward blood flow 18 along the leading end portion 2.

When the forward blood flow 18 encounters a head plug 15 capped to the leading open end of the first helical spring 6, the forward blood flow 18 joins the spiral blood flow 17 to pass beyond the front end portion 2. In this way, an appropriate amount of the blood flow passing along the leading end portion 2 is secured and maintained.

Due to the dynamic pressure from the high speed spiral blood flow 17 and the forward blood flow 18, the resultant force appears to influence the first helical spring 6 and the second helical spring 7 to provide the leading end portion 2 with an advancing force F and a rotational force T.

This is because line diameters of the first helical spring 6 and the second helical spring 7 are thin enough to expand lengthwisely with a minute external force. The expansile force given to the helical springs 6, 7 due to the spiral blood flow 17 is transformed into the advancing force F and the rotational force T against the leading end portion 2.

When manipulating the medical guide wire 1A to insert and indwell the leading end portion 2 to/on the diseased area 13 outside the blood vessel system by means of a handle grip (not shown), a quick and precise manipulation is readily insured with the combined assist of the advancing force F and the rotational force T.

Considering that the blood flows similar to the spiral blood flow 17 and the forward blood flow 18 is slightly present along the leading end portion 2 even within the normal blood vessel, the insertion to the blood vessel is all the more improved when the medical guide wire 1A applies the leading end portion 2 to the blood vessel.

Figure 4:
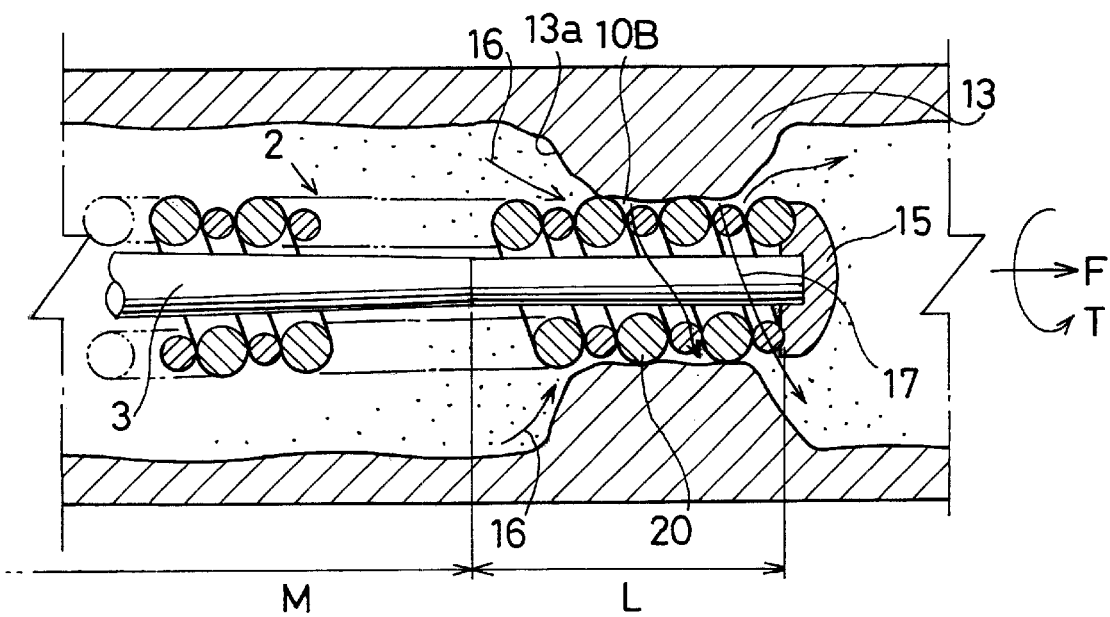
FIG. 4 is a longitudinal cross sectional view of the leading end portion of the medical guide in use.

In this situation, a line diameter of the helical spring 5 wound around the elongated core 3 (circular in cross section) measures 0.072 mm to form the leading end portion 2 (approx. 200 mm in length). The helical diameter (D1) of the first helical spring 6 measures 0.25 mm, and the helical diameter (D2) of the third helical spring 8 measures 0.355 mm FIGS. 3 and 4 show a second embodiment of the invention in which a medical guide wire 1B has a first helical spring 22 and a second helical spring 23 (the former two being equivalent to the helical spring 5) are arranged overlapping each other on the elongated core 3, as opposed to the first, second and third helical springs 6, 7, 8 continuously connected in the first embodiment of the invention.

The first helical spring 22 has the same medial diameter (D3) as a medial diameter that the second helical spring 23 has. The former 22 has a thick diameter line 20, and the latter 23 has a thin diameter line 21. The thick diameter line 20 has a line diameter (d1) greater than a line diameter (d2) that the thick diameter line 20 has.

Line elements of the first helical spring 22 and line elements of the second helical spring 23 are tightly aligned alternately along an axial center 26 in a concentrical relationship each other. The dimensional difference between the line diameters (d1–d2) defines a spiral blood stream path (concave-shaped groove) 10B on outer surfaces of the first and second helical springs 22, 23.

As the same manner as described in the first embodiment of the invention, the high speed spiral blood flow 17 appears along the spiral blood stream path 10B and provides the leading end portion 2 with the advancing force F and the rotational force T.

Since the presence of the thin diameter line 21 can affords to secure the thick diameter line 20 with a greater lead pitch, the leading end portion 2 advances greater per its a single rotation so as to readily indwell on the diseased area 13 when manipulating the medical guide wire 1B.

Figure 5:
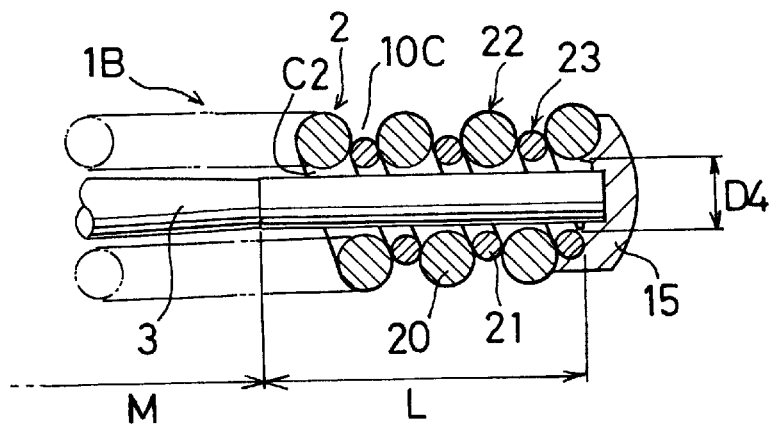
FIG. 5 is a longitudinal cross sectional view of a leading end portion of a medical guide wire according to a third embodiment of the invention.

FIG. 5 shows a third embodiment of the invention in which the second helical spring 23 of FIG. 2 is made shrunken to form a diameter-reduced helical spring so that its inner diameter (D4) is identical to an inner diameter of the first helical spring 22. A greater difference between the thick diameter line 20 and the thin diameter line 21 increases the blood flow running along the spiral blood stream path 10A when the leading end portion 2 gets stuck in the diseased area 13.

Figure 6:
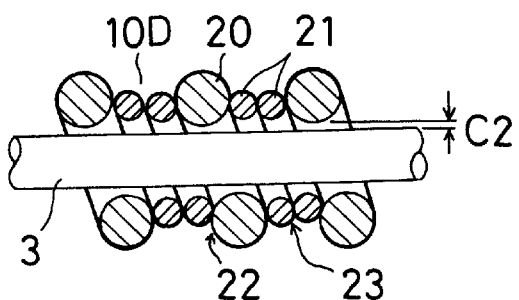
FIG. 6 is a longitudinal cross sectional view of a leading end portion of a medical guide wire according to a fourth embodiment of the invention.

FIG. 6 shows a fourth embodiment of the invention in which another thin diameter line 21 is tightly added concentrically between the line elements (thick diameter line 20) of the first helical spring 22 in the third embodiment of the invention. This further increases the blood flow running along the spiral blood stream path 10D.

Figure 7:
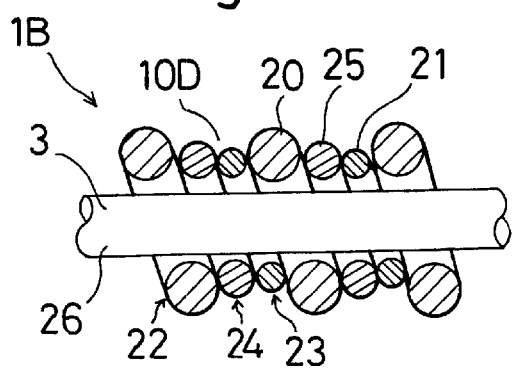
FIG. 7 is a longitudinal cross sectional view of a leading end portion of a medical guide wire according to a fifth embodiment of the invention.

FIG. 7 shows a fifth embodiment of the invention in which either of the two thin diameter lines 21 is replaced with a diameter-increased helical spring 24 in the fourth embodiment of the invention. The diameter-increased helical spring 24 has an intermediary diameter line 25 which has a line diameter greater than the line diameter of the thin diameter line 21, but smaller than the line diameter of the thick diameter line 20.

Figure 8:
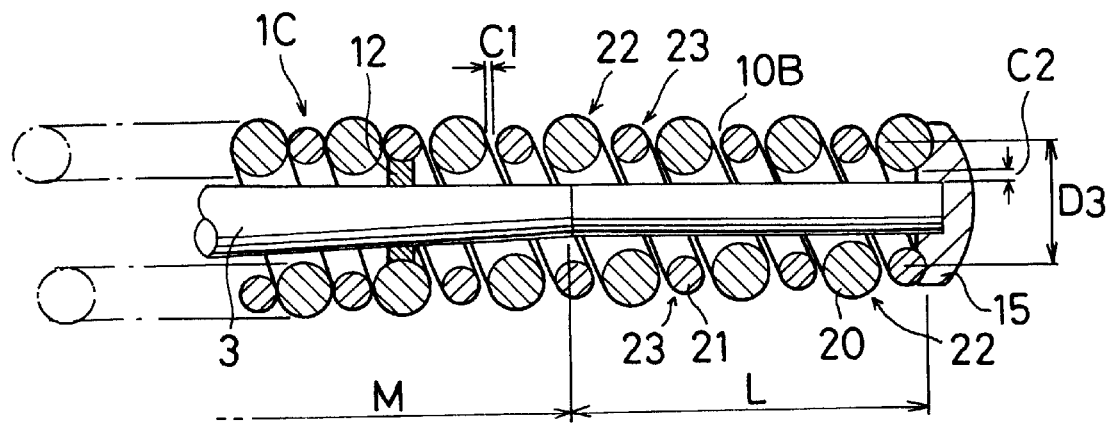
FIG. 8 is a longitudinal cross sectional view of a leading end portion of a medical guide wire according to a sixth embodiment of the invention.

FIG. 8 shows a sixth embodiment of the invention in which a medical guide wire 1C has the gap-stopper 12 provided with the medical guide wire of FIG. 3. Along the lengthwise direction from the gap-stopper 12 to the leading top end of the first helical spring 22, the line gap (C1) is provided between the thick diameter line 20 and the thin diameter line 21. The medical guide wire 1C has a combined advantages that the medical guide wires 1A, 1B (FIGS. 1 and 3) have respectively.

Figure 9:
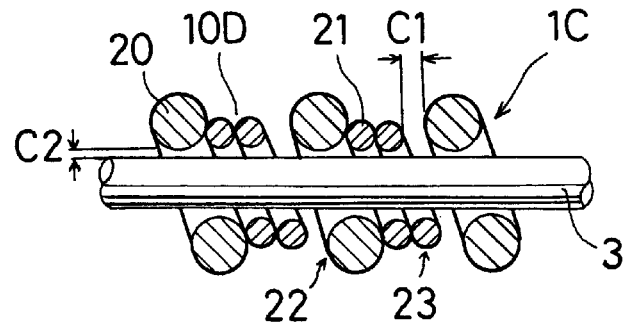
FIG. 9 is a longitudinal cross sectional view of a leading end portion of a medical guide wire according to a seventh embodiment of the invention.

FIG. 9 shows a seventh embodiment of the invention in which the line gap (C1) is provided between the thick diameter line 20 and the thin diameter line 21 of FIG. 6 along the lengthwise direction from the gap-stopper 12 to the leading top end of the first helical spring 22.

As understood from the foregoing description, the tapered helical spring portion 5 is placed around the elongated core 3 (circular in cross section) in the medical guide wires 1A, 1B and 1C. Due to the tapered structure of the helical spring portion 5, the leading end portion 3 readily locate a concave wall of the diseased area 13 to advance into the concave wall. Because the elongated core 3 is circular in cross section, the elongated core 3 readily rotates with the rotational force T due to the blood flow 16 along the spiral blood stream path 10. Due to the line gap (C1), the minute clearance is secured to appear the spiral blood flow 17 without inducing blood clots. The gap (C2) between the elongated core 3 and the helical spring portion 5 are minutely defined so that the gap (C2) would not hinder the spiral blood flow 17 running along the line gap (C1).

While there has been described what is at present thought to be preferred embodiments of the invention, it will be understood that modifications may be made therein and it is intended to cover in the appended claims all such modifications which fall within the scope of the invention.

What is claimed:

1. A medical guide wire comprising:
    an elongated flexible core member which is circular in cross section, the core member having a leading end portion fixed to a head plug and also having a rearward portion;

a helical spring which is concentrically and loosely wound around said core member from the head plug to its rearward portion in the manner that a space appears between said leading end portion and said helical spring;

said helical spring having a diameter-equally-reduced front portion, a diameter-equally-increased rear portion and a tapered portion between said front and rear portions;

a gap stopper provided to stop a gap between a halfway portion of said tapered portion of said helical spring and said core member;

line element turns of said helical spring being tight from said gap stopper to a rearward portion of said helical spring, and line element turns of said helical spring being loose from said gap stopper to the head plug; and a blood stream path provided within said helical spring to be directed from said gap stopper to the head plug when said leading end portion reaches a vascular stricture area.

2. The medical guide wire according to claim 1, wherein a helical spring portion having a thick diameter line and a helical spring portion having a thin diameter line are alternately arranged, and a line gap being present between line element turns of said helical spring portions.

3. The medical guide wire according to claim 1, wherein a helical spring portion having a thick diameter line and a helical spring portion having a thin diameter line are alternately arranged at every two turns of said helical spring, and a line gap being present between line element turns of said helical spring portions.

* * * * *